United States Patent [19]

Erickson et al.

[11] 3,994,876

[45] *Nov. 30, 1976

[54] 6-[α-AMINO-ω-(2,3-METHYLENEDIOXYPHENYL)-ACYLAMIDO]PENICILLANIC ACID DERIVATIVES

[75] Inventors: Raymond C. Erickson; Ronald E. Bambury, both of Cincinnati, Ohio

[73] Assignee: Richardson-Merrell Inc., Wilton, Conn.

[ * ] Notice: The portion of the term of this patent subsequent to Nov. 30, 1993, has been disclaimed.

[22] Filed: July 22, 1975

[21] Appl. No.: 598,135

[52] U.S. Cl. .............................. 260/239.1; 424/271
[51] Int. Cl.² ..................................... C07D 499/68
[58] Field of Search ............................... 260/239.1

[56] References Cited

UNITED STATES PATENTS 2,985,648  5/1961  Doyle et al. .................. 260/239.1

FOREIGN PATENTS OR APPLICATIONS 769,609    7/1971   Belgium .......................... 260/239.1
776,222   12/1971   Belgium .......................... 260/239.1
2,442,867  1967    Japan ............................ 260/239.1

OTHER PUBLICATIONS

Chem. Abstr. vol. 79, 53,355(g) (1973).

Primary Examiner—Gerald A. Schwartz
Attorney, Agent, or Firm—William J. Stein; Eugene O. Retter; George W. Rauchfuss, Jr.

[57] ABSTRACT

Novel 6-[α-amino-ω-(2,3-methylenedioxyphenyl)acylamido]penicillanic acid derivatives are prepared which are useful as antibacterial agents.

6 Claims, No Drawings

6-[α-AMINO-ω-(2,3-METHYLENEDIOXYPHENYL)-ACYLAMIDO]PENICILLANIC ACID DERIVATIVES

FIELD OF THE INVENTION

The penicillin derivatives herein described are particularly useful in the treatment of bacterial infections by oral administration. Methods for their preparation are described.

BACKGROUND OF THE INVENTION

Penicillin-type compounds belong to a well-known family of antibiotics which have been widely used in recent years for the treatment of infectious diseases. A number of useful penicillins have been obtained by varying the substitution at the 6-position of the penicillin nucleus. The search continues, however, for new compounds having a high order of activity and a high degree of stability.

In an effort to improve and expand upon the existing properties of these compounds, efforts have been directed towards improving the substitution at the 6-position of the penicillin nucleus. We have discovered that the presence of an α-amino-ω-(2,3-methylenedioxyphenyl)acylamido moiety at the 6-position of a penicillin nucleus results in certain novel penicillin derivatives having an enhanced activity against one or more gram-positive or gram-negative microorganisms. As antibacterial agents, the compounds of this invention are therapeutically effective in the treatment of infectious diseases caused by gram-positive and gram-negative bacteria in poultry and in animals, including man. Moreover, these compounds are useful as animal feed supplements and as the active ingredient in germicidal preparations employed as surface disinfectants.

PRIOR ART

U.S. Pat. No. 2,985,648 discloses certain alphaamino benzylpenicillanic acid derivatives and is deemed to be the closest art known to applicants. According to the teachings of that patent, this penicillin is prepared by reaction of 6-aminopenicillanic acid with an acylating agent such as the acid chloride, acid bromide, acid anhydride or mixed anhydride of a derivative of D-(—)-α-aminophenylacetic acid in which the amino group is protected by a benzyloxycarbonyl or other suitable protecting group. Upon completion of the acylation reaction, the protecting group is removed from the amino group, such as by reduction with hydrogen in the presence of a catalyst.

SUMMARY OF THE INVENTION

This invention relates to novel 6-[α-amino-ω-(2,3-methylenedioxyphenyl)acylamido]penicillanic acid derivatives. More particularly, this invention relates to 6-[α-amino-ω-(2,3-methylenedioxyphenyl)acylamido]penicillanic acid derivatives which are useful as antibacterial agents and which may be represented by the following formula:

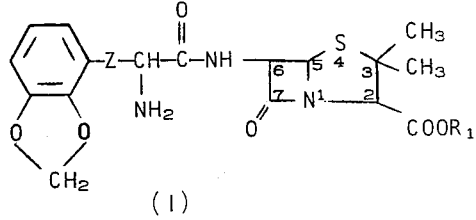

(I)

wherein Z is selected from the group consisting of a sigma bond, methylene and ethylene; $R_1$ is selected from the group consisting of hydrogen, formyloxymethyl and alkanoyloxymethyl in which the alkanoyl group contains from 1 to 5 carbon atoms; and the pharmaceutically acceptable salts thereof.

The compounds of the present invention are prepared by the condensation of an α-amino-ω-(2,3-methylenedioxyphenyl) alkanoic acid having the structure:

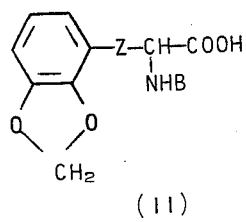

(II)

with a 6-aminopenicillanic acid having the structure:

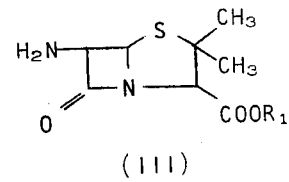

(III)

wherein Z and $R_1$ are as defined above, and B is a blocking group selected from the group consisting of benzyloxycarbonyl, carbomethoxypropen-2-yl, trichloroethoxycarbonyl, p-methoxycarbobenzoxy, p-nitrocarbobenzoxy and the hydrochloric acid salt. These blocking groups are removed after condensation using processes well-known in the art to yield the desired 6-[α-amino-ω-(2,3-methylenedioxyphenyl)acylamido]penicillanic acid derivatives of the present invention (I).

DETAILED DESCRIPTION OF THE INVENTION

As can be seen in formula (I) above all of the compounds of the present invention contain a 1,3-benzodioxole ring at the terminal end of the 6-position acylamido side chains of the penicillin nucleus. For purposes of uniformity of nomenclature, however, all of the compounds described herein shall be designated as 2,3-methylenedioxyphenyl acylamido derivatives. It is to be noted that all of the compounds contain a mandatory amino substituent which is alpha in position to the carbonyl function of the amide group.

The acylamido side chain itself can vary from two to four carbon atoms in length as indicated by the symbol Z. Thus, when Z is a sigma bond, the acetamido side chain is delineated and the compounds are designated as 6-[2-amino-2-(2,3-methylenedioxyphenyl)acetamido]penicillanic acids. The expression "sigma bond" is intended to refer to the ordinary single bond linkage between two adjacent carbon atoms resulting from the overlap of their corresponding obitals. When Z is a sigma bond, a preferred series of compounds is obtained. When Z is methylene, the 6-[2-amino-3-(2,3-methylenedioxyphenyl)propionamido]penicillanic acids are defined, and lastly, when Z is ethylene, the 6-[2-amino-4-(2,3-methylenedioxyphenyl)-butyramido]penicillanic acids are delineated.

The 2-position of the penicillin nucleus is substituted either with a carboxylic acid or a carboxylic acid ester as indicated by the symbol $R_1$. Where $R_1$ is represented by hydrogen, a preferred class of penicillanic acid derivatives is obtained.

The penicillanic acid esters are delineated when the symbol $R_1$ represents either the formyloxymethyl or alkanoyloxymethyl groups. The term alkanoyl as used in this respect includes those groups having a total of from 1 through 5 carbon atoms, as for example, acetyloxy, propionyloxy, butyryloxy, isobutyryloxy, 2-methylbutyryloxy, 3-methylbutyryloxy and 2,2-dimethylpropionyloxy. These esters confer improved properties of absorption upon the molecule and at the same time are physiologically labile. Thus, these esters are readily absorbed from the gastro-intestinal tract and are enzymatically hydrolyzed to the corresponding penicillanic acids, thereby providing excellent oral activity.

The pharmaceutically acceptable salts of the compounds of formula (I) include the non-toxic, carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, vinylamine, N,N'-dibenzylethylenediamine, dihydroabietylamine, N-(lower)alkylpiperidine, and additional amines which have been used to form non-toxic salts with benzylpenicillin. These salts can be prepared using conventional means such as contacting and neutralizing a solution of the carboxylic acid in a polar solvent with a stoichiometric quantity of a base.

Also included as pharmaceutically acceptable acid addition salts are the non-toxic organic or inorganic acid addition salts of the base compounds of Formula (I) above. Illustrative inorganic acids which form suitable salts include hydrochloric, hydrobromic, sulfuric and phosphoric acids as well as acid metal salts such as sodium monohydrogen orthophosphate and potassium hydrogen sulfate. Illustrative organic acids which form suitable salts include mono, di and tricarboxylic acids, as for example, acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicyclic, 2-phenoxybenzoic and sulfonic acids such as methane sulfonic acid and 2-hydroxyethane sulfonic acid. Such salts can exist in either a hydrated or a substantially anhydrous form.

In addition to the non-toxic carboxylic acid salts and the non-toxic acid addition salts of the basic compounds, the term pharmaceutically acceptable salts is taken to include internal salts or zwitterions of the compounds of formula (I) which are amphoteric in nature. Such zwitterions are pharmaceutically equivalent to either of the above mentioned non-toxic carboxylic acid salts or the organic and inorganic acid addition salts and also fall within the purview of the present invention.

Stereoisomerism occurs around the asymmetric α-carbon atom of these acids. The preferred and most active compounds of the present invention are those having the D-configuration at the α-carbon atom in the 6-position side chain and are prepared from the corresponding D (—)-α-amino-ω-(2,3-methylenedioxyphenyl)alkanoic acids (II).

Illustrative specific base compounds encompassed by formula (I) above include:

6-[2-amino-2-(2,3-methylenedioxyphenyl)acetamido]penicillanic acid,
formyloxymethyl 6-[2-amino-2-(2,3-methylenedioxyphenyl)acetamido]penicillanate,
acetyloxymethyl 6-[2-amino-2-(2,3-methylenedioxyphenyl)acetamido]penicillanate,
isopropionyloxymethyl 6-[2-amino-2-(2,3-methylenedioxyphenyl)acetamido]penicillanate,
butyryloxymethyl 6-[2-amino-2-(2,3-methylenedioxyphenyl)acetamido]penicillanate,
pivaloyloxymethyl 6-[2-amino-2-(2,3-methylenedioxyphenyl)acetamido]penicillanate,
6-[2-amino-3-(2,3-methylenedioxyphenyl)propionamido]penicillanic acid,
formyloxymethyl 6-[2-amino-3-(2,3-methylenedioxyphenyl)propionamido]penicillanate,
acetyloxymethyl 6-[2-amino-3-(2,3-methylenedioxyphenyl)propionamido]penicillanate,
propionyloxymethyl 6-[2-amino-3-(2,3-methylenedioxyphenyl)propionamido]penicillanate,
isobutyryloxymethyl 6-[2-amino-3-(2,3-methylenedioxyphenyl)propionamido]penicillanate,
pivaloyloxymethyl 6-[2-amino-3-(2,3-methylenedioxyphenyl)propionamido]penicillanate, 6-[2-amino-4-(2,3-methylenedioxyphenyl)butyramido]penicillanic acid,
formyloxymethyl 6-[2-amino-4-(2,3-methylenedioxyphenyl)butyramido]penicillanate,
acetyloxymethyl 6-[2-amino-4-(2,3-methylenedioxyphenyl)butyramido]penicillanate,
butyryloxymethyl 6-[2-amino-4-(2,3-methylenedioxyphenyl)butyramido]penicillanate,
isobutyryloxymethyl 6-[2-amino-4-(2,3-methylenedioxyphenyl)butyramido]penicillanate, and
pivaloyloxymethyl 6-[2-amino-4-(2,3-methylenedioxyphenyl)butyramido]penicillanate.

The products of the present invention are prepared by reacting 6-aminopenicillanic acid or esters thereof (III) with an α-amino-ω-(2,3-methylenedioxyphenyl)alkanoic acid (II). The 6-aminopenicillanic acid intermediate is a commercially available compound generally obtained by the enzymatic hydrolysis of readily available penicillins. Alternatively, 6-aminopenicillanic acid can be isolated after removal of the natural penicillins from penicillin fermentation broths that have been deprived of side-chain precursors as described, for example, in U.S. Pat. No. 2,985,648.

The α-amino-ω-(2,3-methylenedioxyphenyl)alkanoic acid intermediates are readily prepared as illustrative in Example 2 below. Thus, the compound 2-amino-2-(2,3-methylenedioxyphenyl)acetic acid, hereinafter termed 2,3-methylenedioxyphenylglycine, can be obtained from 2,3-methylenedioxybenzaldehyde by conversion of the latter compound to the corresponding hydantoin derivative and the subsequent hydrolysis thereof.

It will be appreciated that certain of the compounds of this invention exist in various states of solvation as well as in different optically active forms. Ordinarily, the novel compounds of this invention are more active in the D-form of the amino acid than in the L-form or the DL-form Resolution of the racemic α-amino-ω-(2,3-methylenedioxyphenyl)alkanoic acids into their optically active isomers can be effected by conversion to the chloroacetamido derivatives and subsequent hydrolysis thereof using a hog kidney acylase preparation as illustrated in Example 3 below.

In general, the α-amino-ω-(2,3-methylenedioxyphenyl) alkanoic acids are coupled as their functional equivalents in the form of acylating agents for the primary amino group of the penicillanic acid moiety. Functional derivatives used in the coupling reaction include the acyl halides, acid anhydrides, mixed anhydrides and particularly those mixed anhydrides prepared from stronger acids. Additionally, an acid azide or an active ester or thioester, such as p-nitrophenol, thiophenol or thioacetic acid may be used.

The symbol B represents a blocking group of the type used either in peptide syntheses or in any of the numerous syntheses of α-aminobenzylpenicillin from 2-phenylglycine. Particularly useful blocking groups include a proton as with the α-amino hydrochloride salt. Alternatively, a β-keto ester, such as methyl acetoacetate, can be employed as disclosed in Great Britain Pat. No. 1,123,333. The blocked amino acid is converted to a mixed anhydride, as for example with ethyl chloroformate, and then condensed with a 6-aminopenicillanic acid (III). Preferably the blocking group B is selected from the group consisting of benzyloxycarbonyl, carbomethoxypropen-2-yl, trichloroethoxycarbonyl, p-methoxycarbobenzoxy, p-nitrocarbobenzoxy and the hydrochloric acid salt. After coupling, these blocking groups are removed by processes well-known in the art to yield the desired compounds of the present invention. Thus, for example, the benzyloxycarbonyl, p-methoxycarbobenzoxy, and the p-nitrocarbobenzoxy group can be removed by catalytic hydrogenation. Obviously, other blocking groups for the α-amino group can also be used and such groups are deemed to be within the scope of the present invention.

The free α-amino-ω-(2,3-methylenedioxyphenyl)alkanoic acids may also be coupled to 6-aminopenicillanic acid (III) by initially reacting the alkanoic acid with N,N'-carbonyldiimidazole, N,N'-carbonyldi-triazole or a carbodiimide. Especially useful carbodiimides include N,N'-dicyclohexylcarbodiimide, N,N'-diisopropylcarbodiimide or N-cyclohexyl-N'-(2-morpholinoethyl)carbodiimide.

The compound 6-aminopenicillanic acid can be coupled as a free acid. Preferably, however, it is coupled in the form of suitable salts or readily hydrolyzed esters. Suitable salts include the sodium or trialkylammonium salts in which the alkyl group contains from 1 to 5 carbon atoms. Suitable esters include any of those esters disclosed in U.S. Pat. No. 3,284,451 or any of the silyl esters described in U.S. Pat. No. 3,249,622. Following the coupling reaction, these esters are generally removed to yield the products of this invention. In general, the coupling reaction is conducted in the presence of a suitable solvent such as acetone, dioxane, chloroform, ethylene chloride and tetrahydrofuran. In certain instances, mixtures of water and a miscible organic solvent may be advantageously employed. The temperature of the coupling reaction varies from −30° C. to 100° C. with the preferred temperature being at or slightly below room temperature. The reaction time varies anywhere from 15 minutes to as long as 36 hours. Preferably a period of from 1 to 8 hours is employed. Following the condensation reaction, the products are isolated and purified using convential procedures well-known to those skilled in the art.

The compounds of this invention include the various penicillanic acid esters, as indicated by the symbol $R_1$. The preferred esters of this invention include the formyloxymethyl, acetyloxymethyl and the pivaloyloxymethyl esters. These esters are generally prepared by condensing an α-amino--(2,3-methylenedioxyphenyl)alkanoic acid of formula (II) with the corresponding 6-aminopenicillanic ester of formula (III). These esters can be prepared in accordance with the procedures described by Binderup et al., Journal of Antibiotics 24, 767 (1971).

The presence of the α-amino group in the compounds of this invention has a beneficial effect in increasing and enhancing the spectrum of antimicrobial activity against certain gram-negative microorganisms. Additionally, the presence of the α-amino group imparts certain desirable pharmacological characteristics of the molecule thereby enhancing its oral activity.

The novel compounds of the present invention are orally and parenterally active having good antibacterial activity. Thus, they are useful antimicrobial agents having a broad spectrum of antimicrobial activity in vitro against standard laboratory microorganisms used to screen activity against pathogenic bacteria. The antibacterial spectrum and minimal inhibitory concentration (MIC) of typical compounds of the present invention are determined by one or more standard methods. Thus, for example, serial dilutions of the compound being tested are made in tubes of broth or in plates containing an agar medium. Series of tubes of broth or plates of agar containing the different concentrations of the test compound are inoculated with the cultures used in determining th spectrum of activity in vitro. After incubation for 24 hours at 37° C., the inoculated tubes or agar plates are examined for their inhibition of bacterial growth to determine the MIC.

The compounds of this invention possess a broad spectrum of antibacterial activity against both gram-positive and gram-negative organisms, as for example, *Diplococcus pneumoniae, Staphylococcus aureus, Streptococcus pyogenes, Escherichia coli* and *Salmonella schottmuelleri.* They may be used as antibacterial agents in a prophylactic manner, e.g., in cleaning or disinfecting compositions, or otherwise to combat pathogenic infections caused by organisms such as those named above. In general, they may be utilized in a manner similar to other penicillins. Thus, for example, a compound of formula (I) may be used in various animal species in an amount of from about 1 to 200 mg/kg, daily, either orally or parenterally, in single or multiple divided doses to treat bacterial infections. Up to about 600 mg. of a compound of formula (I) or a physiologically acceptable salt thereof may be incorporated in an oral dosage form such as tablets, capsules or elixirs or in an injectable form in a sterile aqueous vehicle prepared according to conventional pharmaceutical practice.

The high in vitro antibacterial activity of the novel compounds of this invention not only makes them useful as pharmacological agents per se, but makes them useful as additives for animal feeds, as well as additives for materials which are subject to microbial deterioration. Thus, these compounds are also useful for their antibacterial effect in soaps, shampoos and in topical compositions for the treatment of wounds and burns. Additionally, these compounds are useful in cleaning or sanitizing compositions for barns or dairy equipment, wherein concentrations comprising about 0.01 to 1% by weight of such compounds can be used admixed with, suspended or dissolved in conventional inert dry or aqueous carriers for application by washing or spraying.

The invention described herein is more particularly illustrated in conjunction with the following specific examples.

EXAMPLE 1

2-(2,3-Methylenedioxyphenyl)acetaldehyde

An ethereal solution of phenyllithium (19.6 ml., 1.02 N) is added in an atmosphere of nitrogen to an ethereal suspension of triphenylmethoxymethylphosphonium chloride (6.84 g., 0.02 mole), prepared according to the procedure of Levine, J. Am. Chem. Soc., 80, 6150 (1958). The mixture is gently heated with stirring until the solution becomes dark red. A solution of 2,3-methylenedioxybenzaldehyde (0.02 mole), prepared according to the procedure of Smidrkal and Trojanek Z. Chem. 1973, 214, contained in 40 ml. of ether, is added via dropwise addition to the above reaction mixture over a period of 15 minutes. The resulting mixture is stirred for an additional 2 hours, filtered, and the filtrate washed with additional ether. The combined filtrate and washings are washed with water and dried over anhydrous potassium carbonate. The ether is removed via evaporation and the residual oil is distilled at 0.1 mm. using a Vigreaux column to obtain the desired vinyl ether. The vinyl ether is briefly stirred with approximately 10 volumes of ether which have previously been saturated with a 72% perchloric acid solution. The ethereal solution is washed with water, washed with a dilute bicarbonate solution, dried over anhydrous magnesium sulfate, filtered, and the ether removed by evaporation. The residual oil is distilled under high vacuum to yield 2-(2,3-methylenedioxyphenyl)acetaldehyde.

Following essentially the same procedure, but substituting 2-(2,3-methylenedioxyphenyl)acetaldehyde for the 2,3-methylenedioxybenzaldehyde, results in the formation of 3-(2,3-methylenedioxyphenyl)propionaldehyde.

EXAMPLE 2

2,3-Methylenedioxyphenylglycine

A sample of 2,3-methylenedioxybenzaldehyde, prepared according to the procedure of Smidrkal and Trojanek, Z. Chem. 1973, 214, is converted to the corresponding hydantoin derivative in accordance with the procedure of Henze and Speer, J. Chem. Soc., 64, 522 (1942), by treatment with ammonium carbonate and potassium cyanide. The hydantoin thus obtained is hydrolyzed with barium hydroxide as described in J. Chem. Soc., 1944, 629, to yield the desired 2,3-methylenedioxyphenylglycine.

Following essentially the same procedure but substituting 2-(2,3-methylenedioxyphenyl)acetaldehyde and 3-(2,3-methylenedioxyphenyl)propionaldehyde in lieu of the 2,3-methylenedioxybenzaldehyde above, results in the formation of 3-(2,3-methylenedioxyphenyl)alanine and 2-amino-4-(2,3-methylenedioxyphenyl)butyric acid, respectively.

EXAMPLE 3

D-2,3-Methylenedioxyphenylglycine

D,L-2,3-methylenedioxyphenylglycine is converted to the chloroacetamido derivative in accordance with the procedure of E. Fisher, Ber., 37, 2486 (1904). Following the procedure of Birnbaum et al., J. Biol. Chem., 194, 455 (1952), the chloroacetylated amino acid is suspended in water and the pH of the suspension is adjusted to 7.5 with 2N lithium hydroxide. The solution is incubated at 37° C. with a hog kidney acylase preparation until hydrolysis of the L-stereoisomer is complete. The pH of the reaction mixture is adjusted to 5.0 and the L-isomer which separates is removed by filtration. The pH of the filtrate is adjusted to 1.0 using concentrated hydrochloric acid and the filtrate extracted with chloroform. The combined chloroform extracts are dried over anhydrous sodium sulfate and evaporated to yield the chloroacetyl derivative of the D-isomer. The chloroacetyl group is removed by hydrolysis using dilute hydrochloric acid. The pH of the hydrolysis mixture is adjusted to 5.5 and the D-2,3-methylenedioxyphenylglycine is collected by filtration.

Following essentially the same procedure the racemic mixtures of 3-(2,3-methylenedioxyphenyl)alanine and 2-amino-4-(2,3-methylenedioxyphenyl)butyric acid are resolved into their D and L-isomers.

EXAMPLE 4

Methyl Acetoacetic Ester Enamine of D-2,3-methylenedioxyphenylglycine, sodium salt D-2,3-methylenedioxyphenylglycine (2.0 mmoles) is dissolved by warming in a solution of 108 mg. of sodium methoxide (2.0 mmoles) in 4.3 ml. of reagent grade methanol. Methyl acetoacetate (255 mg., 0.24 ml., 2.20 mmoles) is added, and the mixture is refluxed for 45 minutes. The methanol is almost completely removed in vacuo. Benzene (5 ml.) is added and distilled to a small residual volume. The addition and distillation of benzene is again repeated to ensure the complete removal of methanol and water. The desired methyl acetoacetic ester enamine of D-2,3-methylenedioxyphenylglycine crystallizes overnight as the sodium salt from the residual volume of benzene, is filtered, washed with benzene, and dried in vacuo.

EXAMPLE 5

6-[D-2-Amino-2-(2,3-methylenedioxyphenyl)acetamido] penicillanic Acid

A solution of 1.66 mmoles of the compound 6-aminopenicillanic acid and 0.23 ml. of triethylamine in 2.5 ml. of water is prepared, with the final pH being 7.4. Acetone (0.85 ml.) is added, and the solution kept at −10° C. A solution of 469 mg. of methyl acetoacetate enamine of D-2-amino-2-(2,3-methylenedioxyphenyl)acetic acid, sodium salt (1.72 mmoles), prepared as in the preceeding Example, in 4.25 ml. of acetone is chilled to −20° C. A microdrop of N-methylmorpholine is added, followed by the slow addition of 198 mg. of ice-cold ethyl chloroformate. Water (0.43 ml.) is added resulting in a turbid solution. The mixture is stirred for 10 minutes at −20° C. The turbid solution of mixed anhydride is added to the solution of 6-aminopenicillanic acid. The clear solution is stirred for 30 minutes at −10° C., raised to room temperature, and acidified with dilute HCl to a pH of 2.0, and with good stirring, maintained at that pH level for 10 minutes. The solution is extracted with 5 ml. of xylene. The aqueous phase is layered with 5 ml. of acetone-methyl isobutyl ketone, and the pH is adjusted to 5.0 with a 1N sodium hydroxide solution and chilled overnight. The resulting crystals are filtered, washed with water and air-dried to yield the desired 6-[D-2-amino-2-(2,3-methylenedioxyphenyl)acetamido] penicillanic acid.

EXAMPLE 6

2,3-Methylenedioxyphenylalanyl chloride hydrochloride

The compound 2,3-methylenedioxyphenylalanine, is treated with hydrogen chloride and phosphorous pentachloride in accordance with the procedure described by Hartcastle et al., J. Org. Chem., 31, 897 (1966) for the preparation of phenylglycyl chloride hydrochloride to yield 2,3-methylenedioxyphenylalanyl chloride hydrochloride.

EXAMPLE 7

6-[2-Amino-3-(2,3-methylenedioxyphenyl)propionamido] penicillanic Acid

To a slurry of 0.01 mole of 6-aminopenicillanic acid in 50 ml. of chloroform is added 4 ml. of N,O-bis-trimethylsilylacetamide. The mixture is stirred until all of the solid dissolves and 0.02 moles of N,N-dimethylaniline is added. The solution is cooled to 5° C. and a 0.01 mole portion of 2,3-methylenedioxyphenylalanyl chloride hydrochloride is added. The mixture is stirred at 5 to 10° C. for approximately 2 hours under an atmosphere of nitrogen. Fifty milliliters of water are added and the pH of the mixture is brought to 2.0 with an aqueous sodium bicarbonate solution. The aqueous phase is separated, decolorized with charcoal, filtered and the pH of the filtrate is adjusted to 4.0 with a dilute sodium hydroxide solution. The resulting solution is chilled and the desired product which forms is removed by filtration, washed with water and acetone, and air-dried to yield 6-[2-amino-3-(2,3-methylenedioxyphenyl)propionamido]penicillanic acid.

Following essentially the same procedure but substituting 2,3-methylenedioxyphenylglycyl chloride hydrochloride and 2-amino-4-(2,3-methylenedioxyphenyl)-butyryl chloride hydrochloride results in the formation to 6-[2-amino-2-(2,3-methylenedioxyphenyl)acetamido]penicillanic acid and 6-[2-amino-4-(2,3-methylenedioxyphenyl)butyramido]penicillanic acid.

EXAMPLE 8

Pivaloyloxymethyl 6-[2-amino-3-(2,3-methylenedioxyphenyl)propionamido]penicillanate hydrochloride Pivaloyloxymethyl 6-aminopenicillanate hydrochloride (0.01 mole) is suspended with sufficient stirring in 50 ml. of anhydrous chloroform at a temperature of about 0° C. Sodium bicarbonate (2.2 grams) is added, followed by the addition of 2,3-methylenedioxyphenylalanyl chloride hydrochloride (0.01 mole). The mixture is stirred for about 4 hours at 0° C., filtered and the filtrate evaporated to dryness in vacuo. The residue is dissolved in water and lyophilized to yield the desired pivaloyloxymethyl 6-[2-amino-3-(2,3-methylenedioxyphenyl)propionamido]penicillanate hydrochloride.

Following essentially the same procedure but substituting formyloxymethyl 6-aminopenicillanate hydrochloride, acetyloxymethyl 6-aminopenicillanate hydrochloride and propionyloxymethyl 6-aminopenicillanate hydrochloride for the pivaloyloxymethyl 6-aminopenicillanate hydrochloride above results in the formation of formyloxymethyl 6-[2-amino-3-(2,3-methylenedioxyphenyl)propionamido]penicillanate hydrochloride, acetyloxymethyl 6-[2-amino-3-(2,3-methylenedioxyphenyl)propionamido]pencillanate hydrochloride and propionyloxymethyl 6-[2-amino-3-(2,3-methylenedioxyphenyl)propionamido]penicillanate hydrochloride, respectively.

We claim:
1. A 6-[α-amino-ω-(2,3-methylenedioxyphenyl)acylamido] penicillanic acid having the formula:

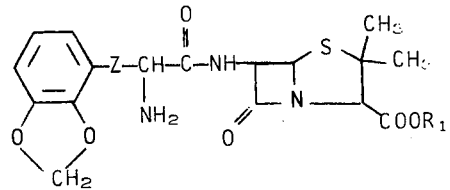

wherein Z is selected from the group consisting of a sigma bond, methylene and ethylene; $R_1$ is selected from the group consisting of hydrogen, formyloxymethyl and alkanoyloxymethyl in which the alkanoyl group contains from 1 to 5 carbon atoms; and the pharmaceutically acceptable salts thereof.

2. A compound according to claim 1 wherein Z is a sigma bond.

3. A compound according to claim 1 wherein $R_1$ is hydrogen.

4. A compound of claim 1 which is 6-[2-amino-2-(2,3-methylenedioxyphenyl)acetamido]penicillanic acid.

5. A compound of claim 1 which is acetyloxymethyl 6-[2-amino-2-(2,3-methylenedioxyphenyl)acetamido]-penicillanate.

6. A compound of claim 1 which is pivaloyloxymethyl 6-[2-amino-2-(2,3-methylenedioxyphenyl)acetamido]penicillanate.

* * * * *